United States Patent [19]

Kessler et al.

[11] Patent Number: 4,985,622

[45] Date of Patent: Jan. 15, 1991

[54] METHOD FOR DETERMINING THE CORROSION RESISTANCE OF DEEP-DRAWABLE IRON SHEETS FOR BODY PARTS OF MOTOR VEHICLES AND APPARATUS FOR PERFORMING THE METHOD

[75] Inventors: Rudolf Kessler, Reutlingen; Winfried Degen, Esslingen; Dieter Oelkrug, Tubingen; Martin Tubach, Reutlingen, all of Fed. Rep. of Germany

[73] Assignee: Daimler-Benz AG, Fed. Rep. of Germany

[21] Appl. No.: 364,607

[22] Filed: Jun. 12, 1989

[30] Foreign Application Priority Data

Jun. 11, 1988 [DE] Fed. Rep. of Germany ....... 3819900

[51] Int. Cl.[5] .............................................. G01J 3/50
[52] U.S. Cl. ..................................... 250/226; 356/406
[58] Field of Search ............... 250/574, 226; 356/237, 356/405–407

[56] References Cited

U.S. PATENT DOCUMENTS

| | | |
|---|---|---|
| 4,095,696 | 6/1978 | Sherwood .......................... 250/226 |
| 4,308,456 | 12/1981 | Van Der Goag et al. ......... 250/226 |
| 4,527,897 | 7/1985 | Okabe ................................ 250/226 |
| 4,592,090 | 5/1986 | Curl et al. ......................... 250/226 |
| 4,647,220 | 3/1987 | Adams et al. ..................... 250/330 |
| 4,653,014 | 3/1987 | Mikami et al. ................... 250/226 |

*Primary Examiner*—Edward P. Westin
*Assistant Examiner*—Khaled Shami
*Attorney, Agent, or Firm*—Evenson, Wands, Edwards, Lenahan & McKeown

[57] ABSTRACT

A method and an apparatus determines a predicted corrosion resistance of deep-drawable iron sheets for body parts of motor vehicles. The method is caarried out with a measuring apparatus comprising one or more light sources with which the iron sheet is irradiated. The reflected light is concentrated by lenses, filtered through filters and the filtered light rays are imaged on a plurality of photoreceivers. The ratios of two respective filter wavelengths are evaluated by a computer from the signals thus obtained. From the values of the quotients of the filter wavelengths, predictions can then be made as to the paint migration values to be expected of the deep-drawable iron sheets painted in a later operation. A simple quality control of the iron sheets supplied by manufacturers for the production of components for motor vehicles can be based on these values.

6 Claims, 2 Drawing Sheets

METHOD FOR DETERMINING THE CORROSION RESISTANCE OF DEEP-DRAWABLE IRON SHEETS FOR BODY PARTS OF MOTOR VEHICLES AND APPARATUS FOR PERFORMING THE METHOD

BACKGROUND AND SUMMARY OF THE INVENTION

The invention relates to a method for determining the corrosion resistance of deep-drawable iron sheets for body parts of motor vehicles, and to an apparatus for performing the method.

Iron sheets manufactured by the steel industry are used on a large scale in the motor vehicle industry for the manufacture of body parts of motor vehicles due to good deep-drawing characteristics. Before being further processed into body parts of a wide variety of configurations, these iron sheets are generally subjected to a phosphating process and then to Painting. The painting operation serves primarily to protect the iron sheets from any subsequent corrosion, and/or to increase the corrosion resistance which naturally exists with this material.

Painting technology for iron sheets has developed a high technical standard particularly with regard to a uniform build-up of paint on the iron sheet. Nevertheless, widely varying behavior of the individual painted body parts as to their corrosion resistance is continually discovered. This varying corrosion resistance in the iron sheets used for the various body parts is attributable to differences in the characteristics of these iron sheets. These characteristics of the iron sheets are visible even through the paint coating of the sheets. Extremely thin oxide coatings on the surface of the sheets are responsible for the variable corrosion quality of the sheets. The thickness and the composition of these oxide layers substantially determine the corrosion resistance of the coated iron sheets.

Various test methods for determining the corrosion resistance of unpainted and painted iron sheets have been disclosed. These methods of determination the future corrosion resistance to be expected of such sheets however are generally very time-consuming. Open air weathering tests of painted sheets last up to twelve months, if these tests are to yield results with any reliability. Even time-accelerated tests under various climatic stresses, such as damp heat tests or salt water spray tests for example, last from several days to several weeks. Moreover, the result obtained from these tests cannot immediately be generalized, nor can it be transferred without distinction to sheets of a different type or from different manufacturers.

Electrochemically operating measuring probes for the determination of the rate of corrosion of metals in corrosive media are disclosed by German Patent Specifications Nos. (DE-PS) 2,030,671, (DE-PS) 2,033,619 and (DE-PS) 2,252,442. However, the application of these procedures to metal sheets presupposes a sampling. The samples require a highly time-consuming conditioning including a cleaning of the sample and also an equilibration so that the effective measuring time for each sample is approximately two hours. As a result, these procedures are not practicable in an on line processing arrangement.

German Patent Specification No. (DE-PS) 2,537,429 relates to a corrosion testing device which operates utilizing a sprayed salt solution. German Published, Unexamined Patent Application No. (DE-OS) 3,405,024 relates to a corrosion testing device which operates with a corrosion mist. However, these methods, in which corrosion of metal surfaces is therefore accelerated by stress climates, require even more time than many of the above-noted methods; up to three weeks in most cases. Moreover, the values obtained by these methods display a low correlation to the corrosion behavior found in practice.

German Published, Unexamined Patent Application (DE-OS) No. 3,418,066 describes a corrosion testing appliance for magnetizable steel sheet utilizing a magnet system which is passed across the steel sheet to create a magnetic flux in the steel sheet. However, this procedure only detects corrosion damage to the sheet which has already developed, and therefore cannot indicate the latent tendency to corrosion which already exists in iron sheets German Published, Unexamined Patent Application No. (DE-OS) 3,339,151 discloses a method and an apparatus for evaluating corrosion protection for a metallic surface, the metallic surface being provided with a surface coating and the extent of a cathodic disbonding being measured German Published, Unexamined Patent Application No. (DE-OS) 3,509,577 also discloses a method and apparatus for testing anti-corrosion layers on a structure stressed mechanically after completion, particularly on the body of a motor vehicle.

A common feature of all these determination methods and/or measuring devices is that, as already explained in detail in some cases, they are both complicated and time-consuming to perform and also involve a large and in some cases complicated apparatus structure.

It is therefore an object of the present invention to provide a method for the determination of the corrosion resistance of deep-drawable iron sheets for body parts of motor vehicles which is simple to perform and utilizes an uncomplicated apparatus technology that provides reproducible measurement results which are consistently obtained rapidly and reliably.

The method and apparatus for determining the corrosion resistance of deep-drawable iron sheets utilize a quantitative determination of the thickness and composition of the oxides on the surfaces of the sheets which, as explained above, substantially determine the corrosion resistance of an uncoated and also of a coated iron sheet.

Other objects, advantages and novel features of the present invention will become apparent from the following detailed description of the invention when considered in conjunction with the accompanying drawings.

DETAILED DESCRIPTION OF THE DRAWINGS

Figure 1:
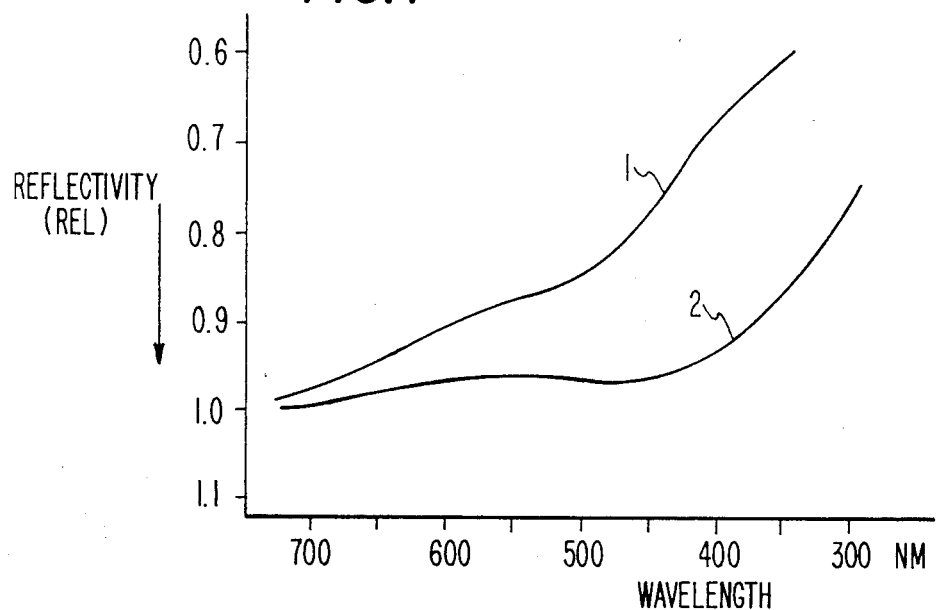
FIG. 1 shows the reflection spectrum of an iron sheet susceptible to corrosion and of an iron sheet corrosion resistance.

In FIG. 1, reference numeral 1 designates a typical reflecting spectrum of an iron sheet susceptible to corrosion and reference numeral 2 designates the reflection spectrum of an iron sheet resistant to corrosion. The wavelength of the light with which the respective sheets are illuminated is indicated in nanometers on the axis of the abscissa. The respective relative reflectivity of the iron sheets is plotted on the axis of the ordinate.

Figure 2:
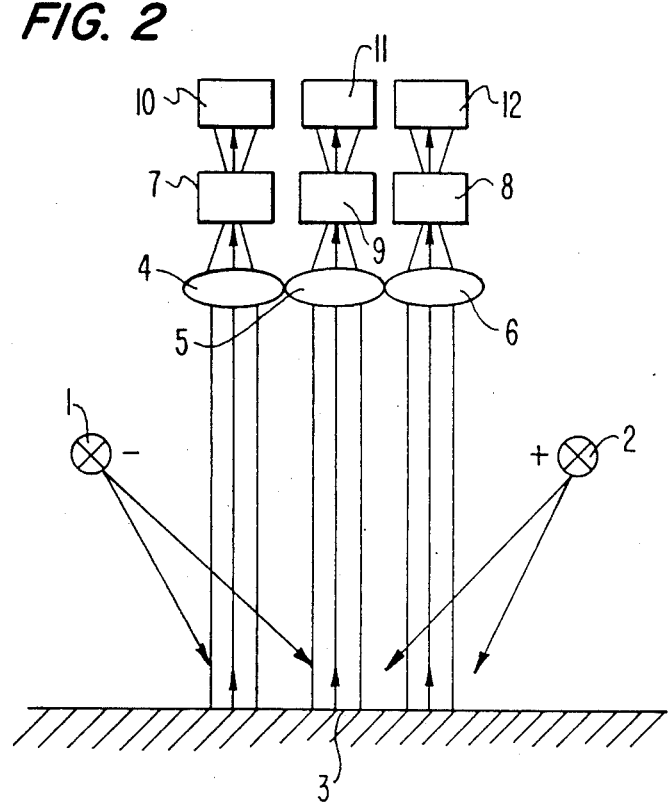
FIG. 2 shows one embodiment of the measuring apparatus for determining the corrosion resistance in accordance with the present invention.

In FIG. 2, two light sources 1, 2 with a stabilized power supply are shown for irradiating a sheet metal sample 3 with radiant energy, for example, visible light, at an angle of about 45°. The light reflected diffusely from the sheet metal sample is passed at right angles through three lenses 4, 5 and 6, concentrated there and then passed to three filters 7, 8 and 9 in order to be imaged subsequently on three photoreceivers 10, 11, 12. The signals produced by the light imaged on the photoreceivers 10, 11, 12 are amplified conventionally. A computer, not shown in the diagrammatic drawing, connected to the three photoreceivers 10, 11, 12 then forms, from the signals of the three photoreceivers 10, 11, 12, the ratios of the reflected light received form the filters 7/9 and 8/9. These calculated quotients constitute the measurement result for the corrosion resistance of the iron sheets.

The choice of the filter wavelengths of the filters 7, 8, 9 used in the apparatus is made after preliminary experiments in which measurements were taken from a metal sheet in a wavelength range T at which existing surface oxide layers strongly absorb the irradiated light, and also in a wavelength range S at which only a slight absorption of the irradiated light by the surface oxides existed. Additionally, measurements were made at a wavelength range N where the measured absorption could not originate from the surface oxides. Then, by forming a ratio of T/N to S/N, the absorption of the reflected light which does not originate from the surface oxides, and which therefore has no influence on the corrosion resistance of the iron sheets, can be eliminated.

By a correlation of the measurement results obtained from the apparatus shown in FIG. 2 in accordance with the method for determining the expected corrosion resistance of the iron sheets with the results of actual long-term open-air weathering experiments with such iron sheets, it is possible to determine the corrosion resistance of iron sheets by analyzing specific frequency ranges of light reflect by oxide layers on the surface of the iron sheet particularly with filters. The filter wavelengths of the filters, and therefore the reflection spectra obtained, preferably lie in a range from 250 to 750 nanometers (nm).

Figure 3:
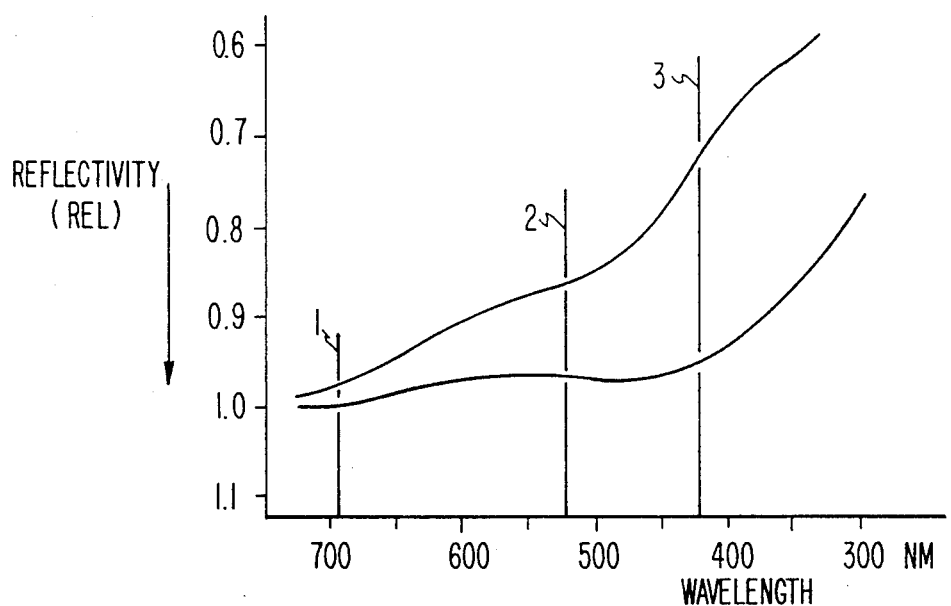
FIG. 3 shows a graph with selected measuring wavelengths.

The position of the selected measurement wavelengths may also be seen from FIG. 3. The wavelength of the irradiated light in nanometers is plotted on the axis of the abscissa, and the respective relative reflectivity on the axis of the ordinate. The line A designates the peak wavelength of an X-filter, the line B the peak wavelength of a Y-filter and the line C the peak wavelength of a Z-filter.

Figure 4:
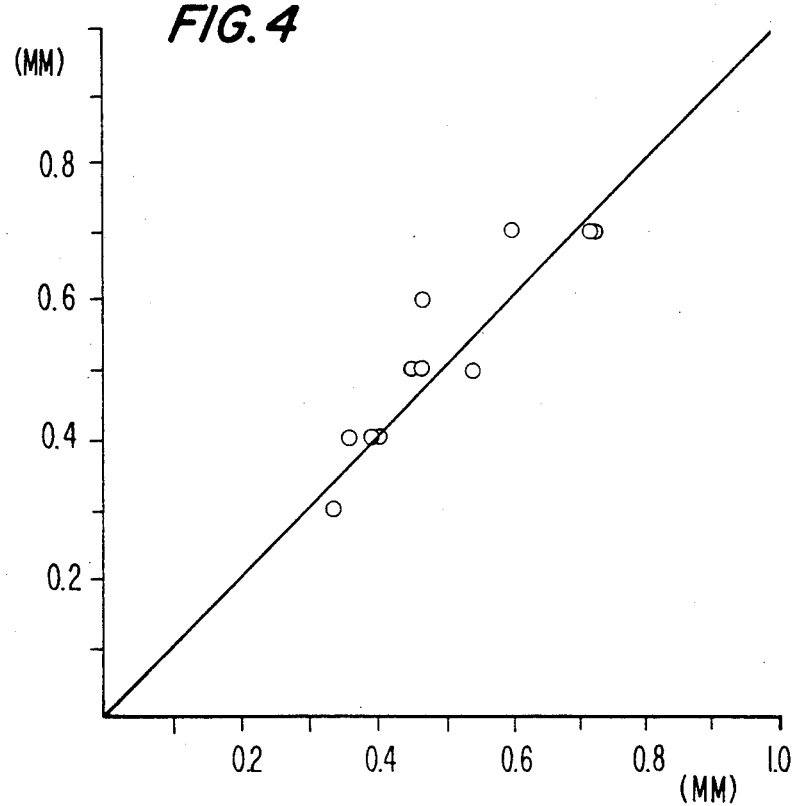
FIG. 4 shows the correlation of measured corrosion resistance values determined in accordance with the present invention and the resistance to corrosion ascertained by long-term weathering.

FIG. 4 graphically illustrates the correlation of measured paint migration values for a painted iron sheet which has been exposed to a 7.5-month open-air weathering test, with the measured values which were obtained for an identical sample of the iron sheet by the apparatus of FIG. 2 in accordance with the method. The measurement values are determined by comparing a reflection spectrum of filter 8 with the reflection spectrum of filter 9 and correlating these values as described in detail hereinafter. This graph indicates the paint migration values determined in each case in millimeters (mm). The measured values of the paint migration in millimeters (mm) are plotted on the axis of the ordinate, and the quotient from the measured values Y of filter 8 and the measured values Z of filter 9 on the axis of the abscissa. The term paint migration in mm is defined here as the superficial extent of the rust patches.

EXAMPLE

An apparatus constructed according to the measuring scheme illustrated by FIG. 2 contains two 12 V/10 W halogen lamps as light sources.

Three converging lenses (3 mm diameter) are installed as lenses.

The filters used are colored glass filters (from Schott) which exhibit the following characteristic date: X-filter: A peak wavelength of about 695 nanometers (nm), a half width of about 60 nanometers (nm) and a transmittency of about 35%. Y-filter: A peak wavelength of about 523 nanometers (nm), half width of about 60 nanometers (nm) and a transmittency of about 25%. Z-filter: A peak wavelength of about 420 nanometers (nm), a half width of about 60 nanometers (nm) and a transmittency of about 35%.

Type BPW 21 photodiodes were used as photoreceivers.

The respective photodiodes are connected through an analog/digital convertor to an APPLE II minicomputer. The computer then forms the quotients from the filters X/Z and Y/Z from the measured values of the three photoreceivers.

The Y/Z values of the still uncoated sheet metal samples were then accordingly measured from samples of typical supplied body sheets. The sheet metal samples were then phosphated and painted as customary and exposed to open-air weathering for approximately 7½ months.

Table I below shows in the first column the values obtained from the quotients of the measured values Y (Y-filter-8) and the measured values Z (Z-filter-9).

The values in millimeters of predicted paint migration determined on the basis of these measurement resulting by means of a correlation equation to be discussed below are listed in the second column.

The paint migration values in millimeters measured after the open-air weathering tests have been performed are plotted in the 3rd column.

The 4th column shows the difference of the values of the paint migration predicted by the method and measured after the open-air weathering test has been performed.

TABLE I

| Quotient of Y/Z Value | Predicted (mm) | Measured Paint Migration (mm) | Difference (mm) |
| --- | --- | --- | --- |
| 1.209 | 0.73 | 0.70 | −0.03 |
| 1.212 | 0.74 | 0.70 | −0.04 |
| 1.149 | 0.61 | 0.70 | +0.09 |
| 1.084 | 0.47 | 0.60 | +0.13 |
| 1.120 | 0.55 | 0.50 | −0.05 |
| 1.084 | 0.47 | 0.50 | +0.03 |
| 1.020 | 0.34 | 0.30 | −0.04 |
| 1.056 | 0.41 | 0.40 | −0.01 |
| 1.083 | 0.47 | 0.50 | −0.03 |
| 1.017 | 0.34 | 0.30 | −0.04 |

TABLE I-continued

| Quotient of Y/Z Value | Predicted (mm) | Measured Paint Migration (mm) | Difference (mm) |
| --- | --- | --- | --- |
| 1.049 | 0.40 | 0.40 | 0.00 |
| 1.033 | 0.37 | 0.40 | +0.03 |

The predicted values of paint migration in millimeters are then obtained by means of a correlation equation:
Paint migration (predicted)=

$$-1.752 + 2.053 \cdot \frac{Y}{Z}$$

The two absolute numerical values contained in the equation have been determined by empirical means.

The advantages achieved by the invention are particularly that an easily handled method is created using a simple apparatus technology for the determination of the corrosion resistance of deep drawable iron sheets. This makes possible a simple and rapid quality control of the sheet metal material delivered by the manufacturers for the production of body parts for motor vehicles.

The use of the method and apparatus is not restricted to the determination of the corrosion resistance of deep-drawable iron sheets. It may be applied generally to the determination of the tendency to corrosion of surfaces of metal structures.

Although the present invention has been described and illustrated in detail, it is to be clearly understood that the same is by way of illustration and example only, and is not to be taken by way of limitation. The spirit and scope of the present invention are to be limited only by the terms of the appended claims.

What is claimed:

1. Method for determining corrosion resistance of a metal sheet comprising the steps of;
   irradiating the iron sheet with radiant energy;
   concentrating radiant energy reflected from the iron sheet;
   filtering the concentrated radiant energy individually through associated filters each having a filter wavelength;
   imaging the filtered radiant energy individually an associated photoreceivers which each generated individual signals; and
   forming ratios of two respective filter wavelengths to determine the corrosion resistance of the metal sheet.

2. Method according to claim 1, wherein the filter wavelengths of the individual filters are in a range from about 250 to 750 nanometers (nm).

3. Apparatus for determining corrosion resistance of a metal sheet comprising:
   a. one or more light sources means for irradiating the iron sheet with light energy,
   b. a plurality of lens means which concentrate light reflected from the sheet surface,
   c. one or more filters means of different filter wavelength which filter reflected, concentrated light,
   d. a plurality of photoreceivers means on which filtered reflected light is imaged, and
   e. computer means, connected to the photoreceivers, for determining the corrosion resistance of the metal sheet.

4. Apparatus according to claim 3, wherein each of the filters of different filter wavelengths has a wavelength in the range from about 250 to 750 nanometers (nm).

5. Apparatus according to claim 3, wherein the half width of the filters is about 50 to 75 nanometers (nm).

6. Apparatus according to claim 3, wherein the metal sheet is made of iron.

* * * * *